(12) United States Patent
Jackson

(10) Patent No.: US 9,881,130 B2
(45) Date of Patent: Jan. 30, 2018

(54) TAGS FOR AUTOMATED LOCATION AND MONITORING OF MOVEABLE OBJECTS AND RELATED SYSTEMS

(71) Applicant: TeleTracking Technologies, Inc., Pittsburgh, PA (US)

(72) Inventor: Stephen S. Jackson, Chapel Hill, NC (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

(21) Appl. No.: 15/681,828

(22) Filed: Aug. 21, 2017

(65) Prior Publication Data

US 2017/0344708 A1   Nov. 30, 2017

Related U.S. Application Data

(63) Continuation of application No. 15/350,534, filed on Nov. 14, 2016, now Pat. No. 9,740,822, which is a continuation of application No. 14/843,682, filed on Sep. 2, 2015, now Pat. No. 9,495,853, which is a continuation of application No. 14/292,042, filed on
(Continued)

(51) Int. Cl.
| | |
|---|---|
| G08B 5/22 | (2006.01) |
| G08B 25/00 | (2006.01) |
| G06F 19/00 | (2011.01) |
| G06K 7/10 | (2006.01) |
| G06K 19/077 | (2006.01) |
| G06Q 10/08 | (2012.01) |
| G06Q 50/22 | (2012.01) |

(Continued)

(52) U.S. Cl.
CPC ....... *G06F 19/327* (2013.01); *G06K 7/10366* (2013.01); *G06K 19/0723* (2013.01); *G06K 19/07749* (2013.01); *G06K 19/07758* (2013.01); *G06Q 10/087* (2013.01); *G06Q 50/22* (2013.01); *G08B 13/2434* (2013.01); *G08B 13/2462* (2013.01)

(58) Field of Classification Search
CPC combination set(s) only.
See application file for complete search history.

(56) References Cited

U.S. PATENT DOCUMENTS 7,250,917 B1 * 7/2007 Thompson ......... G06K 7/10346
340/572.7
7,817,046 B2 * 10/2010 Coveley ............... A61B 5/1113
340/539.12

(Continued)

*Primary Examiner* — Travis Hunnings
(74) *Attorney, Agent, or Firm* — Ference & Associates LLC

(57) ABSTRACT

An example embodiment provides a method, including: receiving, at a tag affixed to a moveable object, a signal to wake the tag affixed to a moveable object; receiving, at the tag affixed to a moveable object, a request from at least one receiver for presence information associated with the moveable object; providing, from the tag affixed to a moveable object, identification information associated with the moveable object; transmitting, from the tag affixed to a moveable object, location data to the at least one receiver; transmitting, from the tag affixed to a moveable object, use state information associated with the moveable object; and returning the tag affixed to a moveable object to a sleep state. Related systems are also provided herein.

16 Claims, 11 Drawing Sheets

Related U.S. Application Data

May 30, 2014, now Pat. No. 9,129,496, which is a continuation of application No. 13/854,577, filed on Apr. 1, 2013, now Pat. No. 8,742,897, which is a continuation of application No. 12/500,168, filed on Jul. 9, 2009, now Pat. No. 8,410,935.

(60) Provisional application No. 61/079,645, filed on Jul. 10, 2008.

(51) Int. Cl.
*G08B 13/24* (2006.01)
*G06K 19/07* (2006.01)

(56) References Cited

U.S. PATENT DOCUMENTS

| | | | | |
|---|---|---|---|---|
| 7,877,166 B2* | 1/2011 | Harwig | ............... | G05D 1/0261 700/245 |
| 8,219,114 B2* | 7/2012 | Larsen | ................. | G01S 5/0226 455/404.2 |
| 8,410,935 B2* | 4/2013 | Jackson | ........... | G06K 19/07749 340/10.1 |
| 8,742,897 B2* | 6/2014 | Jackson | ........... | G06K 19/07749 340/10.1 |
| 8,981,967 B1* | 3/2015 | Shore | ....................... | B64F 5/00 340/945 |
| 9,129,496 B1* | 9/2015 | Jackson | ........... | G06K 19/07749 |
| 9,495,853 B2* | 11/2016 | Jackson | ........... | G06K 19/07749 |
| 9,582,747 B2* | 2/2017 | Saito | ................ | G06K 19/07752 |
| 9,740,822 B2* | 8/2017 | Jackson | ................ | G06F 19/327 |
| 2006/0170530 A1* | 8/2006 | Nwosu | .................... | G06F 21/32 340/5.53 |
| 2009/0058653 A1* | 3/2009 | Geissler | ............ | G08B 13/2462 340/572.1 |
| 2011/0100507 A1* | 5/2011 | Weitzhandler | ......... | B60K 15/04 141/94 |
| 2015/0137955 A1* | 5/2015 | Amador | ............... | G08B 3/1083 340/10.5 |

* cited by examiner

TAGS FOR AUTOMATED LOCATION AND MONITORING OF MOVEABLE OBJECTS AND RELATED SYSTEMS

CROSS REFERENCE TO RELATED APPLICATIONS

This application is a continuation application of U.S. patent application Ser. No. 15/350,534, filed on Nov. 14, 2016, entitled "Tags for Automated Location and Monitoring of Moveable Objects and Related Systems," which is a continuation application of U.S. patent application Ser. No. 14/843,682, filed on Sep. 2, 2015, entitled "Tags for Automated Location and Monitoring of Moveable Objects and Related Systems," which is a continuation of application of U.S. patent application Ser. No. 14/292,042, filed on May 30, 2014, entitled "Rotatable Tags for Automated Location and Monitoring of Moveable Objects and Related Systems," which is a continuation of application of U.S. patent application Ser. No. 13/854,577, filed on Apr. 1, 2013, entitled "Rotatable Tags for Automated Location and Monitoring of Moveable Objects and Related Systems," which is a continuation of U.S. patent application Ser. No. 12/500,168, filed on Jul. 9, 2009, and entitled "Rotatable Tags for Automated Location and Monitoring of Moveable Objects and Related Systems," which claims priority to Provisional Application No. 61/079,645, filed Jul. 10, 2008 and entitled "Rotatable Transponders Having a Housing Within Visible Indicia," the content of each prior application is incorporated herein by reference as if set forth in its entirety.

FIELD

This invention relates to tags and systems related to asset management and, more particularly, to tags and systems for automated location and monitoring of assets.

BACKGROUND

Asset management is becoming a major concern for companies, hospitals, schools, libraries and the like. In other words, as these institutions become larger, it is becoming increasing difficult to manage the location of assets or resources, for example, high-value, mobile assets or resources of which there is a limited quantity available, such as defibrillators. Thus, when one of the many patients in the hospital needs a defibrillator, it is important that the hospital personnel be able to locate a defibrillator for the patient and ascertain its status, for example, in use, available, broken and the like, in a timely manner. Asset management issues may also arise in institutions other than hospitals. For example, a large company may employ far more people than it has portable computers. Thus, when one of the employees needs a portable computer for a business trip, it is important that the employee be able to locate a portable computer and ascertain its status. However, as these institutions become larger, it may become increasingly difficult to monitor the location and status of these high-value, mobile resources. Inefficient asset management can lead to over allocation of funds to purchase more of the limited resources than necessary.

Currently, asset management may include manual asset searches, i.e., send a person to locate the asset, the use of bar codes affixed to the asset or the use of legacy radio frequency tags. However, each of these methods has drawbacks. For example, sending a person to locate an available device may be overly time consuming as well as unsuccessful. Affixing a barcode to the device may not provide any status information, may also be time consuming, unsuccessful and expensive. Legacy radio frequency tags may not provide any device status information, may not be designed for a particular institutions environment, may be expensive and disruptive to install.

A company by the name of Radianse, Inc., of Lawrence, Mass. has attempted to provide a more practical solution to asset management in a hospital environment. Radianse provides indoor positioning solutions (IPS) for healthcare institutions. In particular, Radianse IPSs use long-range active radio frequency identification (RFID) location technology for location and association of people, places and things. Information is shared using web and interface standards such as extensible markup language (XML) and short message service (SMS), and Radianse receivers directly connect to a hospital's existing local area network (LAN).

In particular, to track assets with a Radianse IPS, small, battery-powered transmitters (tags) are attached to mobile medical devices. The tags continuously transmit active RFID information and infrared signals to Radianse receivers plugged into a hospital's existing LAN. The Radianse receivers are standalone devices that are installed in various places in the hospital environment. The RFID information may be received by multiple receivers within a certain perimeter of the tag, but the infrared signal may only be received by the receivers in the same room as the tag due to the nature of infrared. Web-based location software analyzes and displays on a computer screen the exact location based on the RFID information and the infrared signal in real time. Data may also be stored for transfer to any standards-based clinical or hospital information system.

Since the Radianse tag continuously transmits to a reader, the battery life of the tag may only be from about a year to about 16 months, thus, tag replacement may be time consuming and costly. Furthermore, the use of infrared signals to pinpoint the exact location of the mobile medical device may be unreliable as anything placed between the tag and the receiver may block the receiver from receiving the infrared signal. Finally, the Radianse receivers are standalone devices that require installation and integration with the hospital system, which may be burdensome and costly. Accordingly, improved methods of asset management may be desired.

SUMMARY

An embodiment provides a method, comprising: receiving, at a tag affixed to a moveable object, a signal to wake the tag affixed to a moveable object; receiving, at the tag affixed to a moveable object, a request from at least one receiver for presence information associated with the moveable object; providing, from the tag affixed to a moveable object, identification information associated with the moveable object; transmitting, from the tag affixed to a moveable object, location data to the at least one receiver; transmitting, from the tag affixed to a moveable object, use state information associated with the moveable object; and returning the tag affixed to a moveable object to a sleep state.

DETAILED DESCRIPTION

Figure 1A:
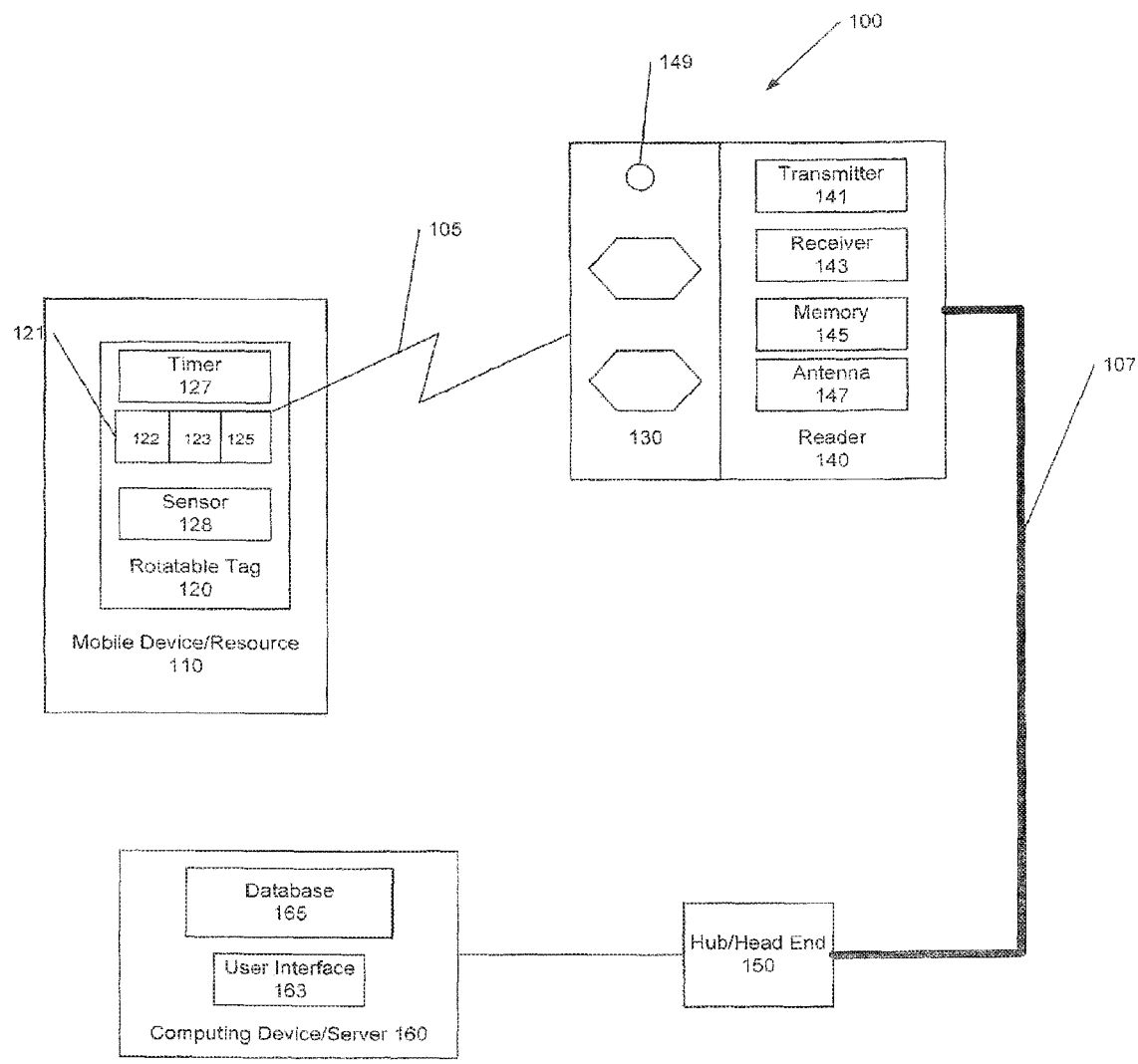
FIG. 1A is a block diagram illustrating a system according to some embodiments of the present invention.

The present invention now will be described more fully hereinafter with reference to the accompanying figures, in which embodiments of the invention are shown. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated selectivity features, integers, steps, operations, elements, and/or components, but do not preclude the presence or addition of one or more other selectivity features, integers, steps, operations, elements, components, and/or groups thereof. As used herein the twin "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention is described below with reference to block diagrams and/or flowchart illustrations of methods, systems, devices and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, the present invention may take the form of a computer program product comprising a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

As discussed above, improved methods of asset management may be desired. Embodiments of the present invention that will be discussed with respect to FIGS. 1A through 13, provide methods, systems, devices and computer program products for providing location information associated with a mobile device. As used herein, "location information" can refer to a single response indicating the presence of a mobile device within a certain perimeter or a more in depth response including coordinates and signal strength. "Presence information" may specifically refer to a response indicating the presence of a mobile device within a certain perimeter of a reader according to some embodiments of the present invention. As further used herein, a "mobile device" refers to a device or resource capable of being moved from one place to another. In some embodiments of the present invention, the mobile device may be a high value mobile asset such as a defibrillator or a laptop computer. However, it will be understood that mobile devices according to some embodiments of the present invention may include library books, files and other lesser value resources without departing from the scope of the present invention. As discussed herein, methods, systems, devices and computer program products according to some embodiments of the present invention may address many of the short falls of conventional methods of asset management.

Devices according to some embodiments of the present invention may be used in the context the RadarFind Real-Time Location System (RTLS). RTLS is a synchronous, real-time tracking system for the location and status of capital assets. It is predominantly used in the healthcare industry, namely for tracking medical equipment and patients in hospitals, however, embodiments of the present invention are not limited to tracking medical equipment.

Intrinsic to the system are tags, for example, rotatable tags or transponders, that interact with other system devices and elements to create a signature of location. Other devices working in conjunction with these precisely timed transponders allow a database to collect information in order to calculate relevant position based on a complex series of precisely timed events as discussed herein. The tags maintain local clocks synchronized to other system devices and therefore are able to deliver more complex data to the RTLS as will be discussed further below.

Referring now to FIG. 1A, a system according to some embodiments of the present invention will be discussed. As illustrated in FIG. 1A, the system 100 includes a mobile device/resource 110, a reader 140, a hub/head end 150 and a computing device/server 160. Mobile devices 110 may be, for example, high-value, portable hospital equipment, such as a hospital bed, an infusion pump, an SCD, an electrocardiogram (EKG) device, a pulse oximeter, a vital signs monitor, a hypothermia machine, a kangaroo pump, a neonatal ventilator or the like. It will be understood that although embodiments of the present invention will be discussed with respect to hospital equipment and hospital environments, embodiments of the present invention are not limited to these environments. For example, some embodiments of the present invention may be used in, for example, school or corporate environments, to monitor the status and location of portable computers, books, files and the like without departing from the scope of the present invention.

As further illustrated in FIG. 1A, the mobile device 110 includes a rotatable tag 120, which is configured to communicate with the reader 140 over a radio frequency RF link 105. It will be understood that although link 105 is discussed herein as an RF link, embodiments of the present invention are not limited to this configuration. The link 105 may be any type of communications link known to those having skill in the art without departing from the scope of the present invention.

Figure 13:
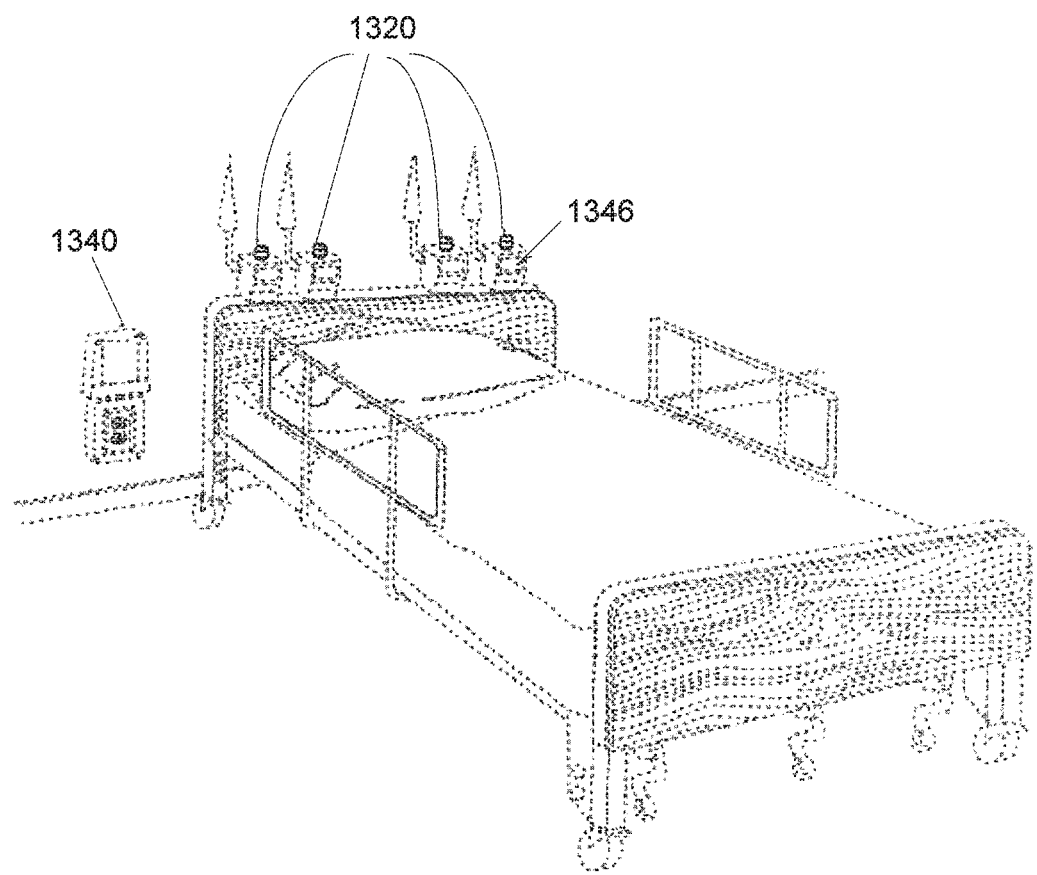
FIG. 13 is a front perspective environmental view including rotatable tags in an exemplary clinical use environment in accordance with some embodiments of the present invention.

The rotatable tag 120 is associated with a mobile device 110 and, in some embodiments of the present invention, the rotatable tag 120 is affixed to the mobile device 110 as illustrated in FIGS. 1A and 13. The rotatable tag 120 may be, for example, an identification tag that may use radio frequencies to communicate. Details with respect to the radio frequency communications are known to those having skill in the art and, thus, only details specific to embodiments of the present invention will be discussed in detail herein. However, as will be understood by those having skill in the art, embodiments of the rotatable tag 120 are not limited to identification tags using radio frequencies to communicate.

In some embodiments, the rotatable tag 120 is configured to receive signals from the reader 140 and transmit signals to the reader 140 over the RF link 105. The rotatable tag 120 is configured to transmit information responsive to a request from the reader 140. It will be understood that in some embodiments of the present invention, the rotatable tag may just transmit or may transmit and receive (transponder) without departing from the scope of the present invention. Furthermore, the rotatable tag 220 can transmit autonomously, responsively or synchronously without departing from the scope of the present invention.

In some embodiments of the present invention, the rotatable tag 120 is battery powered. To conserve battery life, the rotatable tag 120 (tag) is in a sleep mode most of the time. Thus, the battery used in rotatable tags 120 according to some embodiments of the present invention may last significantly longer than those of conventional tags. For example, the battery life of a battery in a rotatable tag 120 according to embodiments of the present invention may be about 6 years or more. Accordingly, the cost of affixing rotatable tags 120 to mobile devices 110 may be reduced as well as battery replacement costs.

In particular, the rotatable tag 120 is configured to periodically wake up from the sleep mode and listen for a request (beacon signal), for example, a request for presence information, from the reader 140. If the rotatable tag 120 receives the request when it is awake, the rotatable tag 140 is configured to transmit the requested presence information to the reader 140. In some embodiments of the present invention, the rotatable tag 120 may be configured to have different levels of "awake" and "sleep." In these embodiments of the present invention, the rotatable tag 120 may be configured to fully awake before responding to the request from the reader 140.

If, on the other hand, the rotatable tag 120 does not receive the request within a predetermined period of time, the rotatable tag 120 may return to sleep mode. The reader 140, which will be discussed further below, may be configured to transmit the request multiple times to ensure that the rotatable tag 120 will receive the request when it is awake. As further illustrated in FIG. 1A, the rotatable tag 120 may include a timer 127. The timer may be, for example, a back-off timer which is configured to indicate how long the rotatable tag 120 can stay awake before going back to sleep. The timer 127 may be set to one or more microseconds so as not to consume a lot of the battery life. The timer 127 may also be used for collision avoidance between similarly located rotatable tags 120. For example, if a first rotatable tag has a back-off timer set to 2 microseconds (μs) and another rotatable tag may have a back-off timer of 4 μs, the likelihood that the information they are transmitting to the reader 140 will intersect may be reduced.

The timer 127 may also be used to indicate when the rotatable tag 120 should wake up. It will be understood that more than one timer may be provided without departing from the present invention. In other words, rotatable tags 120 may have more than one sleep mode. The rotatable tag 120 may be configured to detect that it has not received a request from the reader 140 in a significant period of time, for example, ten minutes or more. This may occur when a mobile device 110 having the rotatable tag 120 affixed thereto is transported in an ambulance with a patient and is no longer within range of a reader. Once the rotatable tag 120 realizes it has not received a request in a significant period of time, a value of the wake up timer may be increased so that the rotatable tag wakes up more infrequently, for example, every 3 minutes. This feature may enable the battery life to be further increased.

According to some embodiments of the present invention, the time at which the rotatable tag 120 will wake up may be determined randomly using, for example, time and frequency division multiplex control by prime coefficients for pseudo arbitrary channel efficiency or determined at specific times, by use of a disciplined oscillator and time-slot assignments. Using this method may increase the likelihood that the rotatable tag 120 and the request (beacon) from the reader 140 will not be out of synch; i.e., decrease the likelihood that every time the rotatable tag wakes up, the request has just come or is going to come after it goes to sleep. Thus, according to some embodiments of the present invention, the rotatable tag wakes up randomly and, therefore, the likelihood of the rotatable tag and the request being unsynchronized may be reduced.

As further illustrated in FIG. 1A, the rotatable tag 120 may further include indicia 121 to indicate a state of the mobile device 110. In some embodiments of the present invention, the indicia 121 may be color-coded, which may allow detection of the state of the device from across the room, which may be useful when searching for an available device. In some embodiments of the present invention, the rotatable tag may have a cylindrical shape as illustrated in FIG. 1B.

In some embodiments, the indicia 121 may include three portions, a red portion 122 may be red, which may indicate that the mobile device 110 is out of service, a blue portion 123, which may indicate that the mobile device 110 is in use and a green portion 125, which may indicate that the mobile device 110 is available or not in use. These colors may be visible from across the room and, therefore, returning to the console to determine the state of the mobile device 110 may not be necessary. It will be understood that although the indicia illustrated in FIG. 1A includes three states, embodiments of the present invention are not limited to this configuration. Zero to two or four or more states may be indicated without departing from the scope of the present invention.

In some embodiments of the present invention, the rotatable tag 120 may be configured to operate on multiple frequencies. In other words, the rotatable tag 120 is preloaded with different channel banks, A, B, C and so on. If the hospital happens to be using one frequency for another operation, then the frequency on which the rotatable tag 120 receives and/or transmits can be changed so as not to interfere with current hospital frequency use. This feature may allow embodiments of the present invention to adapt to the hospitals' existing frequency and not to cause any disruption in the current operations thereof.

Figure 1B:
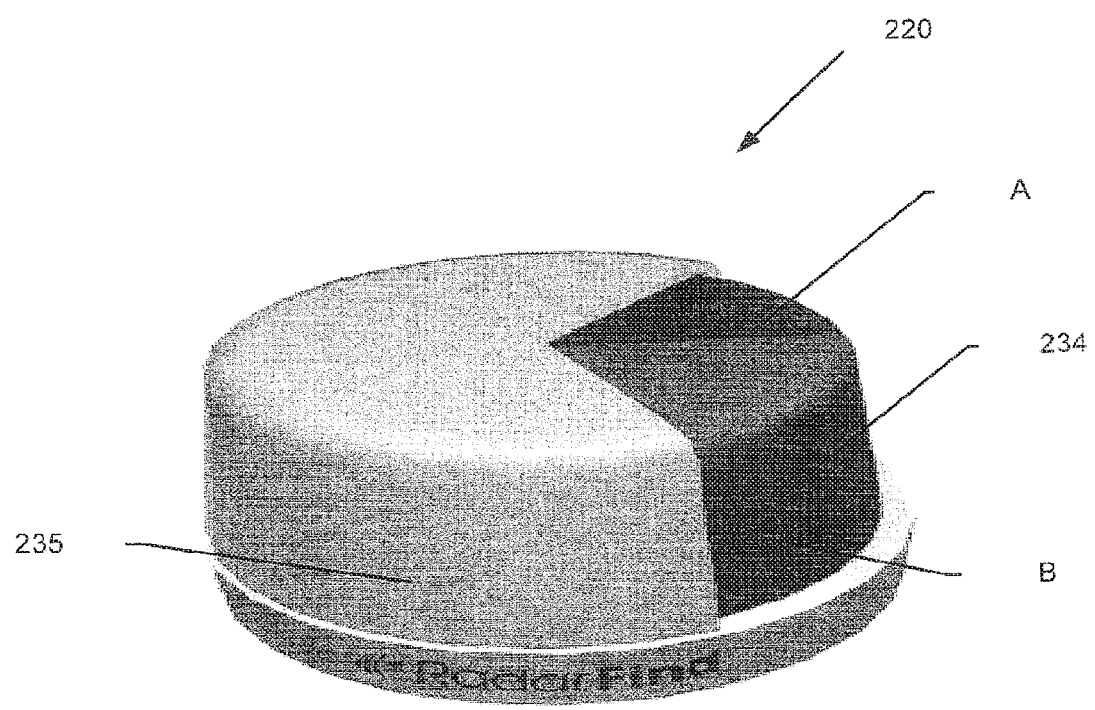
FIG. 1B is a perspective view of rotatable tags according to some embodiments of the present invention.

Referring now to FIG. 1B, some embodiments of the present invention are directed to the cylindrical housing and rotatable exterior component of the tag 220. Although embodiments of the rotatable tag 220 discussed herein have a cylindrical housing, embodiments of the present invention are not limited to this configuration. Some embodiments of the present invention provide a tag 220 having an external portion made of, for example, plastic, generally in multiple, snap-together pieces. The tag 220 may include, but is not limited to, a battery-powered electronic apparatus, a radio transceiver, and micro circuitry. A tag 220 in accordance with some embodiments of the present invention is affixed to a capital asset or object that is generally movable. The tag 220 can be affixed to the movable object using any method known to those having skill in the art. As illustrated in FIG. 13, an exemplary view of an environment in which the tags 220 can be used, by affixing the tags 1320 to assets 1346, and then tracking the tag locations, the assets 1346 can be located within the RTLS using communications between the tags 1320 and the reader 1340.

Referring again to FIG. 1B, in some embodiments of the present invention, the tag 220 may be configured to indicate the use state of the object to which the tag 220 is affixed, generally through a switch or switches, which may be activated by pushing, turning, twisting or sliding one or more pieces of the tag housing to reveal different-colored/patterned indicia. Colors, form, and meaning of the indicia are subjective to each use case. For example, the different patterns/colors on the tag 220 may indicate that the object to which the tag 220 is affixed is in use, available, needs cleaning, needs service or the like.

In certain embodiments of the present invention, the tag 220 may be configured to transmit information about itself and its surroundings. In these embodiments, the tag 220 may include sensors (128 FIG. 1), such as temperature sensors, motion sensors, humidity sensors, gas sensors, carbon monoxide sensors, accelerometers, gyroscopes and the like. Thus, a tag in accordance with some embodiments of the present invention may be placed in the helmet of a fireman and may be used to detect a position of the fireman when he enters a fire scene. For example, the sensors in the tag may be used to indicate if the fireman is standing up or lying down inside the fire scene. If it is determined that the fireman is in distress, the tag 220 may be further used to locate the fireman in the fire scene.

FIG. 1B is a three-dimensional visualization illustrating a rotatable tag housing with a three-state indicator in accordance with some embodiments of the present invention. Although the rotatable tag of FIG. 1B illustrates three states, embodiments of the present invention are not limited to this configuration. The rotatable tags in accordance with some embodiments of the present invention may indicate any number of states without departing from the scope of the present invention, the number of which is only limited by how small a sliver can be made on the tag. This may be an advantage over conventional, for example, rectangular tags, on which there may be a practical limitation of to the number of states that can be shown.

Figure 11:
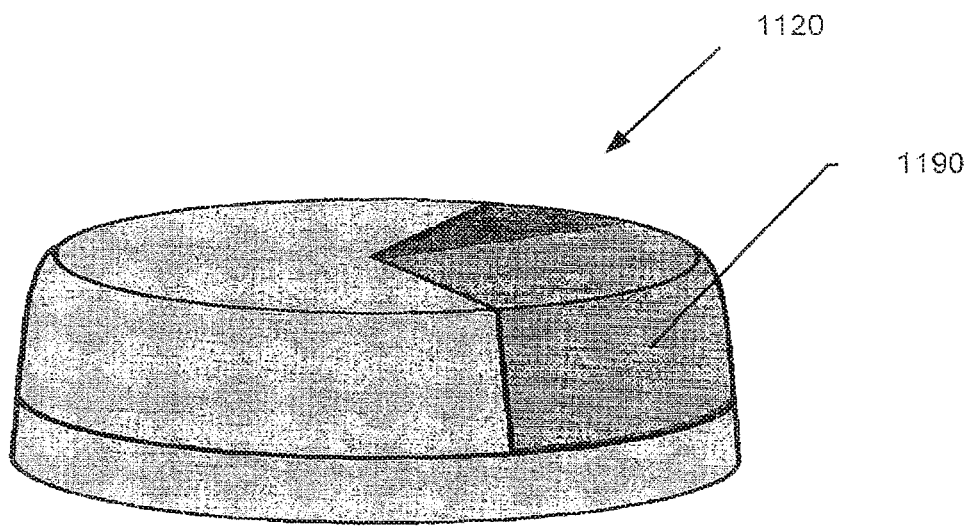
FIG. 11 is a diagram illustrating a transponder with the window in place in accordance with embodiments of the present invention.
Figure 12:
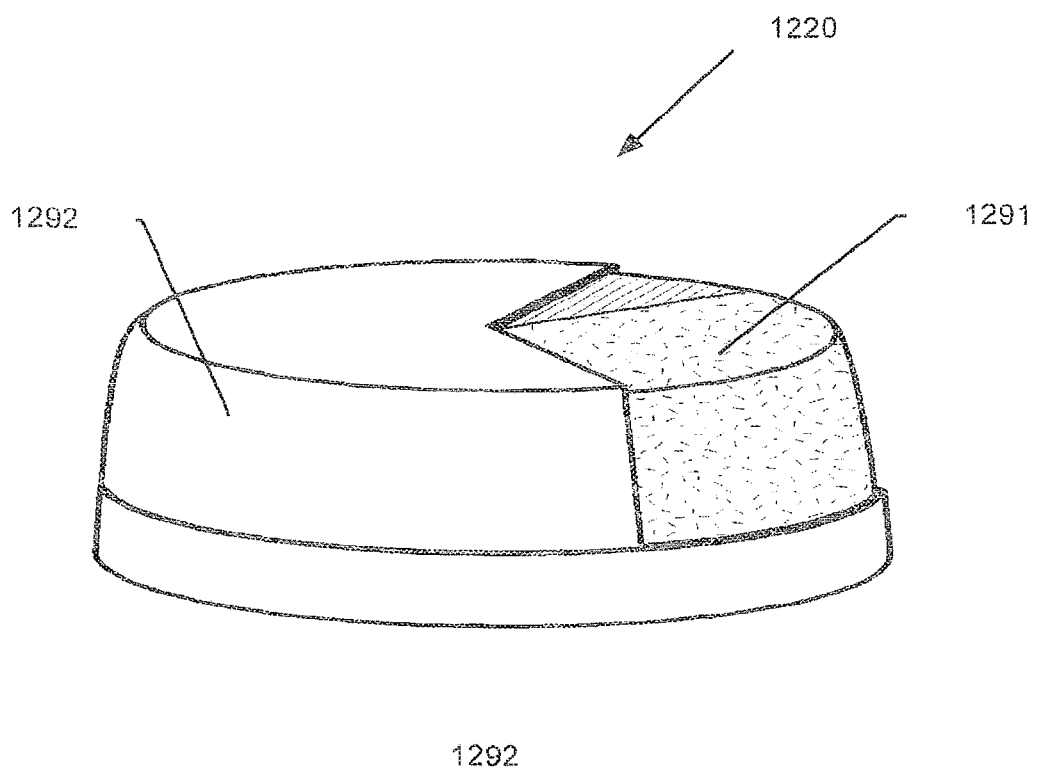
FIG. 12 is a cross-section illustrating an inner cylinder versus the outer cylinder of a transponder as if the indicia window was removed in accordance with some embodiments of the present invention.

FIG. 11 is a diagram illustrating a tag with a window 1190 in place in accordance with some embodiments of the present invention. FIG. 12 is a cross-section illustrating an inner cylinder 1291 versus the outer cylinder 1292 of a tag as if the indicia window was removed in accordance with some embodiments of the present invention.

As illustrated in FIGS. 1B and 11 through 12, the tag 220, 1120 and 1220 may have a cylindrical shape, which may allow both local (visual) and remote (electronic) indication of the state of the attached device. In other words, the rotatable tag 220, 1120 and 1220 is further configured to indicate at least one state of the attached device such that the at least one state of the attached device is discernable from a distance.

Figure 2:
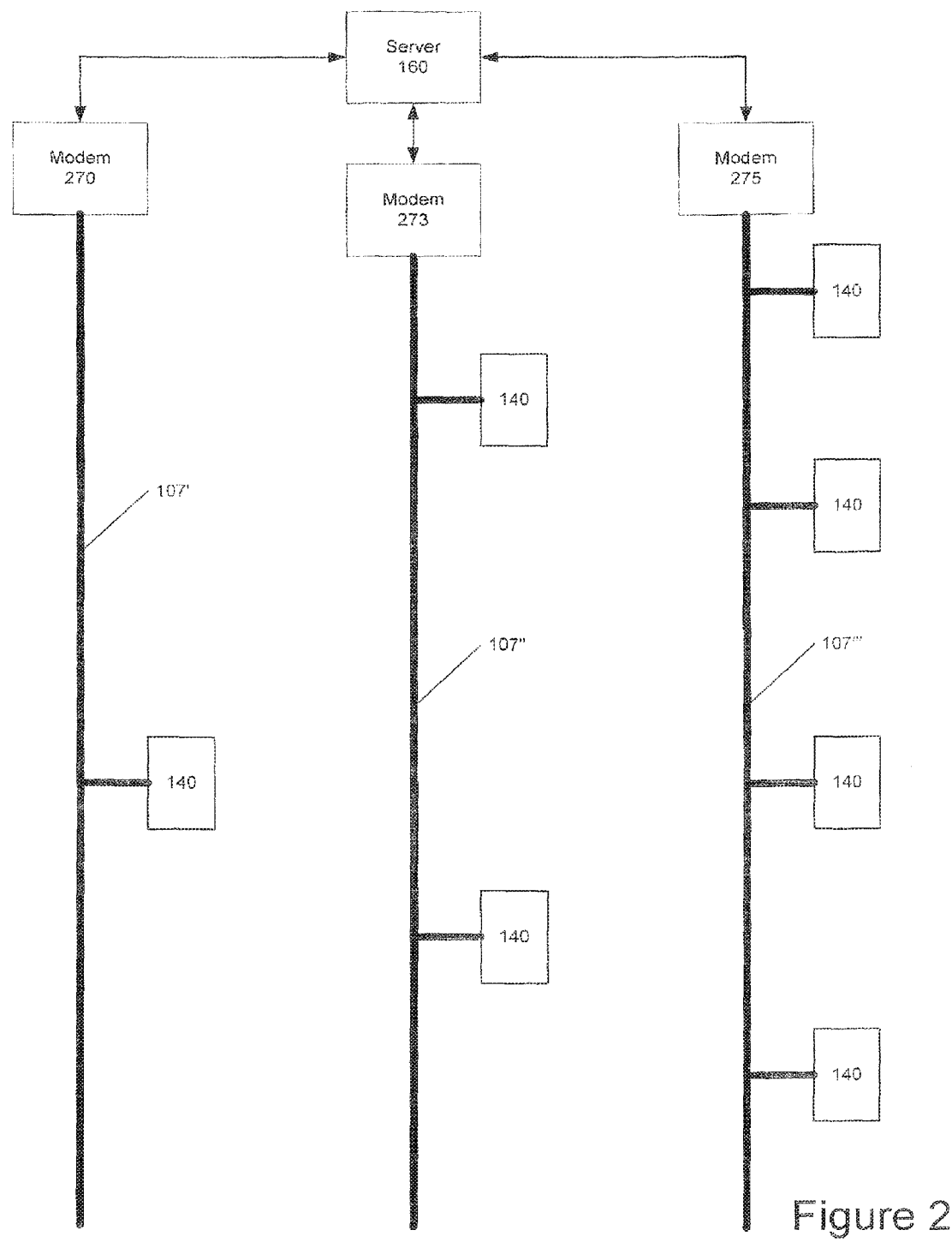
FIG. 2 is a block diagram illustrating a head end and a three phase power line according to some embodiments of the present invention.

As illustrated, for example, in FIG. 2, the housing of the tag 220 may include first and second portions. The first portion 234 may include at least two different patterns A and B. As used herein, "patterns" refer to patterns, colors or anything that can be used such that a difference between the slivers can be discerned by the eye. The second portion 235 is configured to be placed on top of the first portion 234 and has a translucent or transparent portion (1190 FIG. 11). The second portion 235 is configured to rotate and reveal one of the at least two different patterns through the translucent portion 1190 of the second portion 235. In some embodiments, each of the at least two patterns is indicative of a state of the object discussed above.

It will be understood that although FIG. 11 illustrates the second portion 235 being a contiguous piece having a translucent portion 1190, embodiments of the present invention are not limited to this configuration. For example, as illustrated in FIG. 1, the second portion 235 may be configured to have a wedged portion removed and to reveal the different patterns through the wedged portion without departing from the scope of the present invention.

The cylindrical shape of the tags 220, 1120 and 1220 illustrated in FIGS. 1B, 11 and 12 may also allow the interior volume for the electronics package to be increased, i.e., the form of the housing may provide an increased volume. As used herein, an "increased volume" refers to more volume than a conventional tag having a conventional form factor and thus allowing more electronics to be included in the tag relative to conventional tags. Furthermore, the contact area between the tag and the attached device may be reduced, i.e., the housing may occupy a relatively small amount of surface area on the attached device. As used herein, "relatively small amount of surface area" refers to less surface area than a conventional tag having a conventional form factor. The cylindrical shape may also provide the rotating capability to change and reveal indicia as discussed above.

Rotatable tags 220, 1120 and 1220 are intrinsically safe such that they can be used in an oxygen rich environment. Thus the tags 220 do not have any exposed electrical contacts and, therefore, will not spark. Furthermore, the oxygen in the air will not ruin the tag or the tag contact.

As discussed above, some embodiments of the present invention provide a packaging innovation for a tag that incorporates a cylindrical rotating component 235 and a fixed component 234. The rotating component shares an axis with the fixed component, and the rotating component may include a feature 1190 that reveals a plurality of indicia. As discussed above, the indicia may be colored or patterned panels, or lights, or some combination thereof without departing from the scope of the present invention.

The cylindrical packaging according to some embodiments of the present invention may allow an interior container volume to be increased, while reducing the surface area of the object to which the tag is attached. Increased interior volume enables more room for electronic circuitry, for power source or sources, antenna or antennas and the like relative to conventional form factors. These internal electronics communicate via at least radio signals, and communications include at least data indicating a plurality of states that correspond to the rotational position of the packaging. Internal electronics also co-correspond to the plurality of indicia on the package, or to the lack of and/or the indeterminate state of any rotational position information and/or indicia.

Some embodiments of the present invention provide data about the device to which it is connected or the vicinity in which the device is located. Such data may pertain to the use state of the attached device or vicinity.

Conventional tags may take up too much physical area on the attached device because they are configured in inadequate geometric shapes and aspect ratios. For example, tags having a rectangular shape can be an inefficient use of space as it is not ideal for the volume of interior tag components. The form factor of the rotatable tag in accordance with some embodiments of the present invention may allow the volume of the tag to be increased or possibly maximized, while reducing or possibly minimizing the amount of space the tag occupies on the device.

Other related devices have been miniaturized in various ways by constraining the internal volume of space. Such form factors limit the capabilities of internal electronics, constrain usability by people based on the fixed minimum size of human fingers, and reduce the ability to show indicia without consuming electrical power. Furthermore, the form factors and construction of related devices may inadvertently collect residual chemical and biological contaminants.

Tags according to some embodiments of the present invention may provide a cylindrical form factor that reduces the possible contact area with the item to which it is attached. Geometrically, a cylindrical shape may achieve an increased volume above a surface. Devices in accordance with some embodiments of the present invention rotate in order to change or reveal the indicia. Although the outside shape of the tag might not appear to be a cylinder, the interior volume would appear as a cylinder, therefore the device rotates about its vertical axis. Furthermore, the ability to clean devices in accordance with some embodiments of the present invention from residual chemical and biological contaminants may also be increased, as the tag may include a cylindrical solid and therefore may be relatively easy to wipe off.

Use of tags in accordance with some embodiments of the present invention may enable the adopter to receive and utilize statistics on the use of the device to which the tag is attached. This statistical data may be highly valuable because it allows the adopter to discern the value of the assets to which the present invention is attached, and whether, for example, to buy more or fewer of the devices based on usage and device-state patterns. The data generated by some embodiments of the present invention and system components may also ensure improved utilization of capital assets because the assets are in the right place at the right time and in suitable condition for use.

Adding efficiency to the delivery of health care has both economic and social implications. Hospital staff is better focused on improved patient care and mission critical services. Costs for the rental, purchase, and maintenance of hospital equipment are greatly reduced and money is saved.

Use of embodiments of the present invention and its location and status tracking system may be a tremendous asset to determine the utilization of equipment and capital assets. By tracking the location and status of medical devices, users may know exactly when each medical device is being used, or if and why it is not being used. Users could possibly employ a smaller number of like devices and use them more frequently or more thoroughly, thus receiving a greater return on investment based on using capital assets more efficiently.

Some embodiments of the RTLS include the following attributes or features: non-disruptive installation, coverage for entire facility, status tags, longest battery life for tags, tamper-resistant base with multiple mounting options, telemetry monitoring, no interference with existing WiFi networks, relatively easy to use, easily scalable, low hospital IT impact, no interference with other systems in the hospital, display of real-time device status and location, interacts with existing databases and low total cost of ownership.

Referring again to FIG. 1, as discussed above, the rotatable tag 120 communicates with the reader 140 (transcoder) over an RF link 105. In some embodiments of the present invention, the reader 140 may transmit to the rotatable tag 120 using auto-synchronous on/off keying. This type of communication signal typically requires very little processing and power and, therefore, may further conserve the battery life of the rotatable tag 140. Furthermore, in some embodiments of the present invention, the rotatable tag 120 may communicate with the reader 140 using frequency shift keying. As discussed above, the reader 140 may be configured to transmit a request for presence information to the rotatable tag 120 multiple times to ensure the reception of the request at the rotatable tag 120 when the rotatable tag 120 is awake.

As illustrated in FIG. 1A, readers 140 according to embodiments of the present invention are integrated with the existing infrastructure of the hospital. For example, the reader 140 of FIG. 1A is integrated with a non-critical outlet 130 already present in the hospital. Thus, readers 140 according to embodiments of the present invention may use the power lines 107 already present in the hospital and do not require a complicated installation procedure. In other words, the housing, wiring and the like are already present in the hospital. The use of existing infrastructure may significantly decrease the cost of implementing asset management according to some embodiments of the present invention, which is typically very important to the customer. It will be understood that although embodiments of the present invention are illustrated as being integrated with power outlets, embodiments of the present invention are not limited to this configuration. For example, a reader 140 may be integrated in an Exit sign or any device having access to the power lines or other resilient power source without departing from the scope of the present invention.

As further illustrated in FIG. 1A, the reader 140 may include a transmitter 141, a receiver 143, a memory 145 and an antenna 147. The reader 140 is configured to communicate with the hub 150 over the power lines 107. Thus, the reader 140 according to some embodiments of the present invention is configured to communicate with the rotatable tag 120 over an RF link 105 and with the hub 150 over the power line 107.

In some embodiments of the present invention, the reader 140 is a layer 2 processor, i.e. it may not be configured to process any information received from the rotatable tag 120. Thus, the transmitter 141 of the reader 140 is configured to transmit a request for presence information (beacon signal) to the rotatable tag 120 and the receiver 143 of the reader 140 is configured to receive the presence information from the rotatable tag 120 and store the information received in the memory 145. The memory 145 may be a first in first out (FIFO). The receiver 143 of the reader 140 may be further configured to receive a request for the stored information from the hub 150 over the power line 107 and the transmitter 141 of the reader 140 may be further configured to transmit the stored information to the hub 150 over the power line 107 responsive to the request.

In some embodiments of the present invention, the presence information may be stored in the memory 145 with a time stamp. The time stamped information can be erased at will, which may aid in compliance with Health Insurance Portability and Accountability Act (HIPAA) regulations. Thus, the information can be deleted and the actual time of deletion may be recorded.

The reader 140 may only transmit information to the hub 150 in some embodiments upon request, for example, responsive to a poll from the hub 150. In further embodiments the hub 150 communicates with the reader(s) 140 via a radio frequency communications link. In some embodiments of the present invention, the information provided to the hub 150 responsive to the poll may include a name of the reader, the temperature at the reader, a current time, and a dump of all the information stored in the memory 145 (FIFO). The temperature may be provided as a precautionary measure to possibly avoid, for example, long term circuit damage or a fire. For example, if the temperature at the reader 140 is elevated, it may indicate a problem with the circuitry and, thus, may be addressed before a larger problem arises.

Figure 1C:
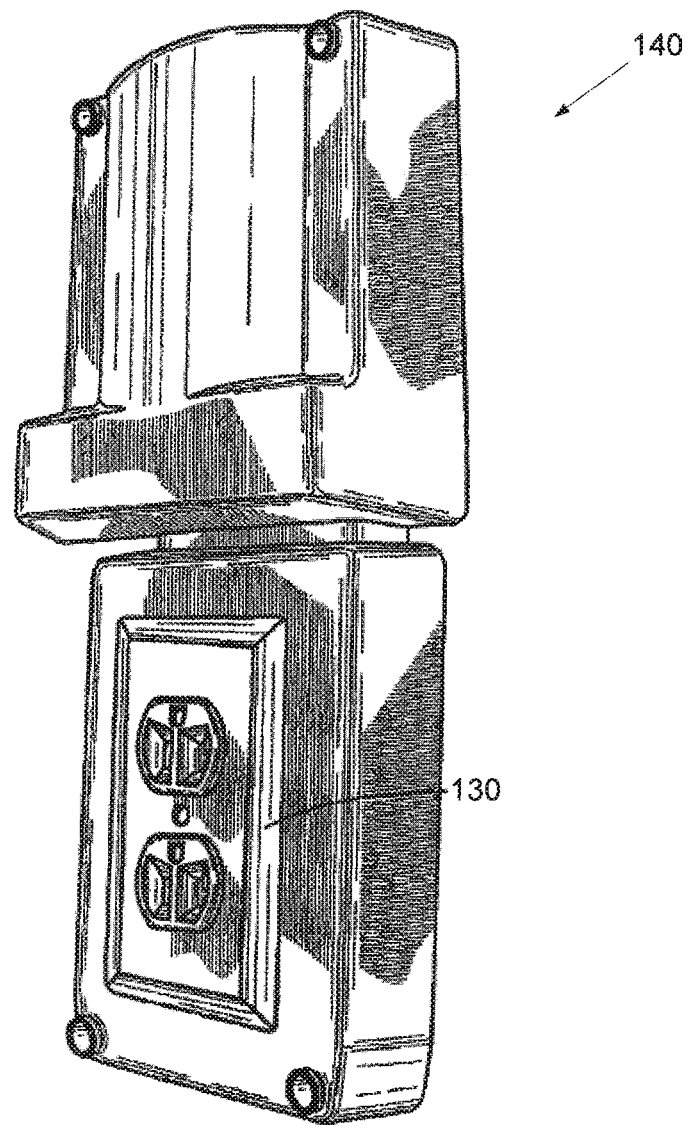
FIG. 1C is a three-dimensional visualization illustrating a rotatable tag housing with a three-state indicator in accordance with some embodiments of the present invention.

In some embodiments of the present invention, a reader 140 may be coupled to a light source 149, for example, a light emitting diode, as illustrated in FIG. 1A. The light source 149 may be mounted outside the outlet so as to be visible to hospital personnel. These particular readers 140 may be mounted near ingress/egress points in the hospital to provide an added level of security against, for example, theft of a mobile device. In other words, these readers 140 may operate similar to security tags provided on items sold in retail stores. For example, the reader 140 may be installed in an outlet and the light source 149 may be mounted in a visible location outside the outlet. Accordingly, if someone tries to remove a mobile device 110 having an rotatable tag 120 affixed thereto from the hospital, the light source 149 may be configured to flash to indicate that a mobile device 110 was being removed from the hospital. In some embodiments, an audible alarm may also be configured to sound. It will be understood that the light source 149 is an optional feature of readers 140 according to embodiments of the present invention. However, all readers 140 may be capable of operating in conjunction with a light source 149 discussed above. A perspective view of readers 140 integrated with an outlet 130 according to some embodiments of the present invention is illustrated in FIG. 1C.

Figure 4:
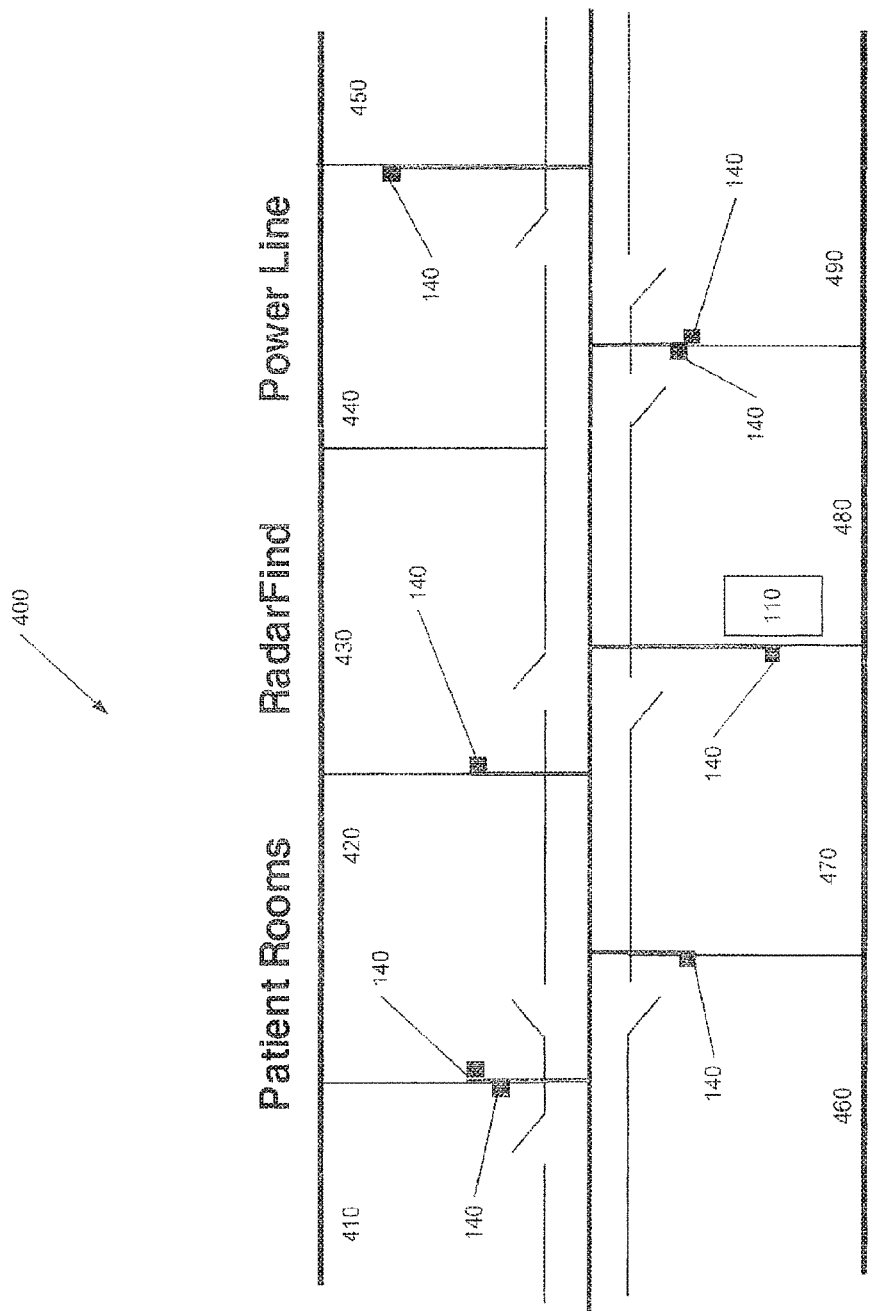
FIG. 4 is a diagram of a hospital floor equipped with devices according to some embodiments of the present invention.

As further illustrated in FIG. 1A, the reader 140 further includes an antenna 147. As discussed in the background of the invention, conventional tags use infrared signals to pinpoint a location of the mobile device 110. However, this method may be very unreliable. Antennas 147 according to embodiments of the present invention may allow the specific location of the mobile device 110 to be pinpointed based on signal strength, which may be much more reliable than infrared as signal strength does not depend on a clear line of sight. In particular, as illustrated in FIG. 4, readers 140 may be positioned in multiple hospital rooms 410 through 490 on a single hallway 400. A mobile device 110 having an rotatable tag 120 according to some embodiments of the present invention may be positioned in a hospital room 480 but may be closer to the reader 140 in hospital room 470. Using an antenna according to embodiments of the present invention having a defined range, when the readers 140 send out requests (beacon signals) to the rotatable tag(s) 120 and the rotatable tag(s) 120 respond, the signal strength of the response will appear stronger to the reader 140 in hospital room 480 in which the device sits than to the reader 140 in hospital room 470. As used herein, a "defined range" refers to a controlled range so as to allow the discovery of a mobile device within the defined range to indicate a location/presence of the mobile device within a certain distance of the reader 140. Thus, according to some embodiments of the present invention signal strength may be used to pinpoint the location of the mobile device 110, which may be more reliable than the use of infrared as discussed above. Signal processing is known to those having skill in the art and, therefore, the details of the signal processing will not be discussed further herein.

Referring again to FIG. 1A, as discussed above, the hub 150 communicates with the reader(s) 140 over the power lines 107. The hub 150 may be positioned in an electrical closet at the hospital. The hub 150 is configured to obtain stored information from the reader(s) 140. Thus, the server transmits a request for stored information to the reader(s) 140 and receives the stored information from each of the readers 140. As discussed above, the hub 150 may further receive a name of the reader 140 in which the information was stored, a temperature around the reader and a current time. The hub 150 may store the received information in a database 165. Although the database 165 is illustrated as being a part of the computing device/server 160 in FIG. 1A, embodiments of the present invention are not limited to this configuration.

As illustrated in FIG. 2 and will be understood by those having skill in the art, a power line 107 typically has three phases −120° (107'), 0° (107") and 120° (107'''). Thus, outlets 130 and, therefore, readers 140 integrated therewith, may be coupled to any one of the three phases 107', 107" and 107''' of the power line 107. The lines of each phase are isolated from starting loads on the other lines. As illustrated in FIG. 2, according to some embodiments of the present invention, a power line modem 270, 273 and 275 is placed on each of the three phases 107', 107" and 107''' of the power line 107. A request for stored information is transmitted from each of the power line modems 270, 273 and 275 at the simultaneously, which may significantly reduce the crosstalk between the lines. It will be understood that transmission from each of the power lines "simultaneously" refers to transmission at the same time plus or minus one or more phase differences. Furthermore, all of the readers 140 may transmit a response to the request at the same time. As illustrated in FIG. 2, some of the lines have more readers 140 attached thereto than others. In particular, a first phase 170' has a single reader 140 attached thereto, a second phase 170" has two readers 140 attached thereto and the third phase 170''' has four readers attached thereto. Thus, the lines having a smaller number of readers attached thereto have to wait until the line with the most readers attached thereto has received its last response before the process can be repeated. As further illustrated in FIG. 2, the information from each of the readers 140 may be stored in a database at the server 160 or at a computing device separate from the server 160. In some embodiments of the present invention, the server 160 is attached to the network clock so as to allow accurate timing of events.

Finally, as further illustrated in FIG. 1A, a computing device/server 160 includes a user interface 163 and the database 165. Although the computer device and server are illustrated as one unit in FIG. 1A, embodiments of the present invention are not limited to this configuration, these may be separate units without departing from the scope of the present invention. The database 165 may be customized according to customer preferences. As further illustrated in FIG. 1A, the computing device/server 160 is configured to communicate with the hub 150 using, for example, an Ethernet connection. The user interface 163 may include, for example, a graphical user interface (GUI). This GUT may be used to locate the mobile device 110 that is needed by the hospital personnel. For example, the GUI may contain a list of all the mobile devices 110 having rotatable tags 120 affixed thereto. The type of device needed may be clicked on, which may then begin the process according to embodiments of the present invention for location of the needed mobile device 110. In particular, the hub 150 may be asked to poll the readers 140 to determine the location of the mobile device 110. As discussed above, the stored information received from the reader(s) 140 may be stored in the database 165 which may reside at the computing device/server 160.

It will be understood that although FIG. 1A includes a single mobile device 110 having an rotatable tag 120 affixed thereto, a single reader 140 integrated with an outlet 130, a single a hub/head end 150 and a single computing device/server 160, embodiments of the present invention are not limited to this configuration. One or more of each of these elements may be included in the system 100 without departing from the scope of the present invention.

As illustrated in FIG. 1A, the system 100 according to some embodiments of the present invention includes four elements, a database 165, a hub 150 (head end), a reader 140 (transcoder) integrated with an outlet 130, and an rotatable tag 120 (identification tag) affixed to a mobile device 110. Thus, systems according to some embodiments of the present invention combine Ethernet, power line, and RF communications.

Some embodiments of the present invention may use a voice XML session that interacts with the XML text to implement various functionalities of embodiments of the present invention. For example, hospital personnel trying to locate a mobile device 110 can call a device configured according to embodiments of the present invention. When the device receives the call, the X, Y and Z coordinates of the hospital personnel may be received as well as the extension from which they are calling. Thus, the positional information provided for the mobile device 110 located for the hospital personnel will not only be where the mobile device is, but will be the closest available mobile device relative to the hospital personnel's current position.

In some embodiments of the present invention, the rotatable tag may only be configured to transmit presence information, i.e., in these embodiments of the present invention, the rotatable tag may not receive requests from the readers. Rotatable tags according to these embodiments of the present invention may be configured to keep track of, for example, a baby born at the hospital to reduce the likelihood that the baby will be stolen from the neonatal unit. Accordingly, rotatable tags according to these embodiments of the present invention may include three frequency banks: "A" for the beacon (request), "B" for the beacon response (presence information), and "C" for the real time information with respect to patients and babies. It will be understood that rotatable tags according to these embodiments of the present invention may used in conjunction with other objects and resources, for example, books in a library. Embodiments of the present invention may be configured to look for a particular tag (rotatable tag) and if the rotatable tag is located an alert may be transmitted.

Although embodiments of the present invention are discussed herein as having readers 140 integrated with outlets 130, embodiments of the present invention are not limited to this configuration. For example, some embodiments of the present invention may be implemented without the rotatable tag. In particular, the radio in the transcoder (reader) may be replaced with different sensors, for example, microphones, spy chips, humidity sensors, temperature sensors, and the like. A spy chip may be used to locate electronic bugs in government buildings and the device may be configured to transmit an alert whenever a bug, a Bluetooth transceiver or a cell phone that shouldn't be there is found. These embodiments of the present invention may also be configured to locate when and where the unwanted activity is happening so that it can possibly be stopped.

Figure 3:
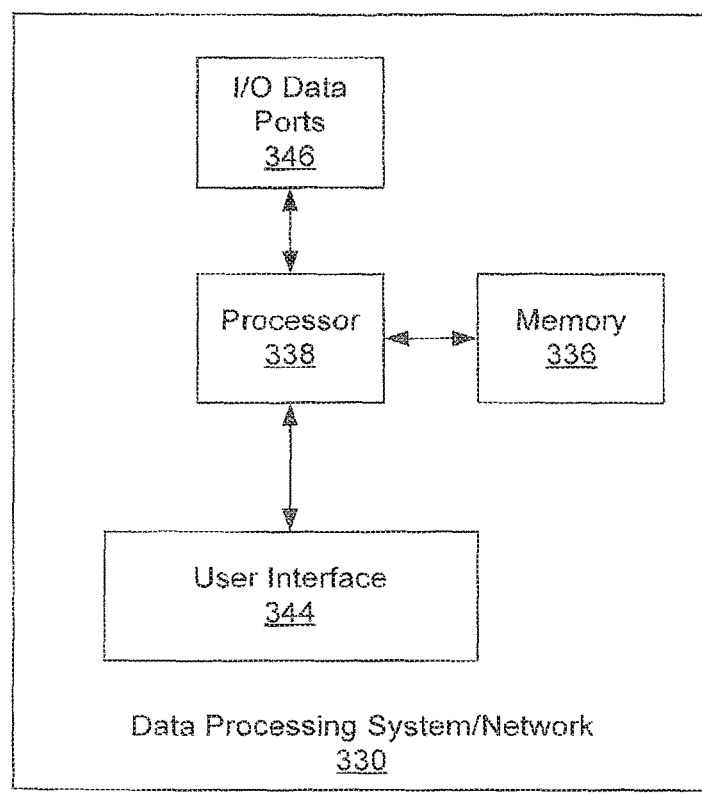
FIG. 3 is a block diagram of a data processing system suitable for use in devices according to some embodiments of the present invention.

FIG. 3 illustrates an exemplary embodiment of a data processing system 330, which may be included in devices, for example, computing device 160 and hub 150, in accordance with some embodiments of the present invention. The data processing system 330 may include a user interface 344, including, for example, input device(s) such as a keyboard or keypad, a display, a speaker and/or microphone, and a memory 336 that communicate with a processor 338. The data processing system 330 may further include an I/O data port(s) 346 that also communicates with the processor 338. The I/O data ports 346 can be used to transfer information between the data processing system 330 and another computer system or a network using, for example, an Internet Protocol (IP) connection. These components may be conventional components such as those used in many conventional data processing systems, which may be configured to operate as described herein.

The processor 338 can be any commercially available or custom enterprise, application, personal, pervasive and/or embedded microprocessor, microcontroller, digital signal processor or the like. The memory 336 may include any memory devices containing the software and data used to implement the functionality of the data processing system 330. The memory 336 can include, but is not limited to, the following types of devices: ROM, PROM, EPROM, EEPROM, flash memory, SRAM, and DRAM.

Furthermore, the memory 336 may include several categories of software and data used in the system, for example, an operating system; application programs; input/output (I/O) device drivers; and data. As will be appreciated by those of skill in the art, the operating system may be any operating system suitable for use with a data processing system, such as OS/2, AIX or zOS from International Business Machines Corporation, Armonk, N.Y., Windows95, Windows98, Windows2000 or WindowsXP, or Windows CE from Microsoft Corporation, Redmond, Wash., Palm OS, Symbian OS, Cisco IOS, VxWorks, Unix or Linux. The I/O device drivers typically include software routines accessed through the operating system by the application programs to communicate with devices such as the I/O data port(s) 346 and certain memory 336 components. The application programs are illustrative of the programs that implement the various features of the system and preferably include at least one application that supports operations according to embodiments of the present invention. Finally, the data may represent the static and dynamic data used by the application programs, the operating system, the I/O device drivers, and other software programs that may reside in the memory 336.

Operations according to various embodiments of the present invention will now be further described with reference to the flowchart illustrations of FIGS. 5 through 10.

Figure 5:
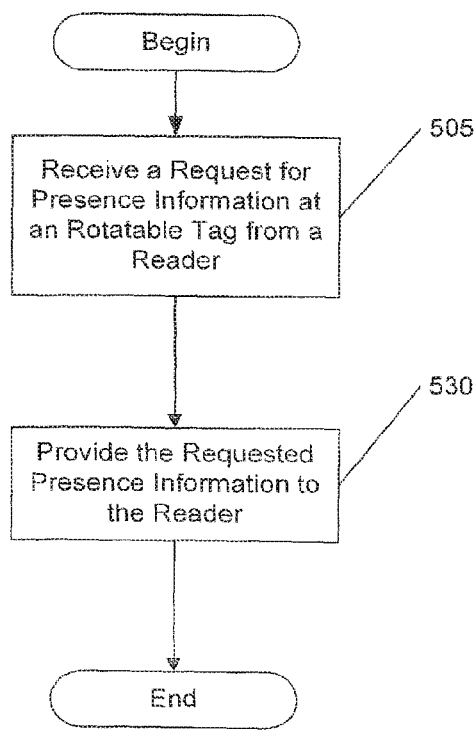
FIGS. 5 through 10 are flowcharts illustrating operations according to various embodiments of the present invention.

Referring first to FIG. 5, methods for providing location information associated with a mobile device according to some embodiments of the present invention will be discussed. Operations begin at block 505 by receiving a request for presence information at an rotatable tag associated with the mobile device. The request may be received over an RF link. The rotatable tag may be, for example, an identification tag and the "presence information" may be a response indicating the presence of the rotatable tag. It will be understood that in some embodiments of the present invention, the request may be for "location information", which may be a more detailed response including location coordinates. The request or beacon signal may be received from a reader, for example, a transcoder, within a predetermined proximity of the rotatable tag. The reader may be integrated with the power outlets and communicate over the existing power lines. The requested presence information may be provided to the reader responsive to the request for presence information (block 530). The requested information may be provided over the RF link.

Figure 6:
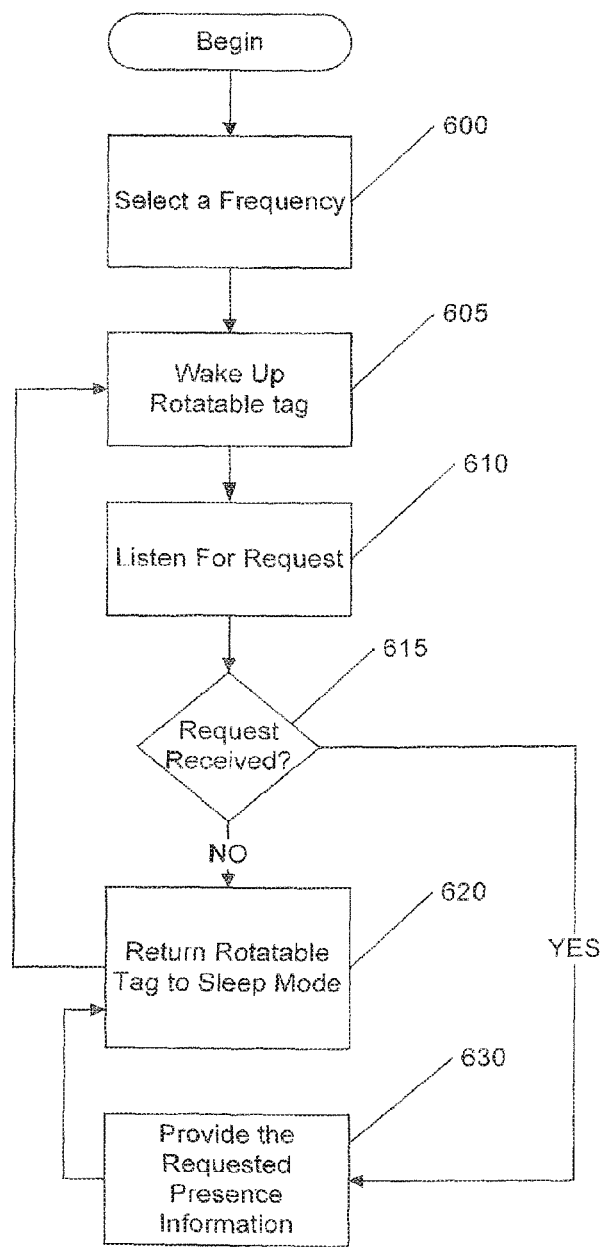

Referring now to FIG. 6, methods for providing location information associated with a mobile device according to some embodiments of the present invention will be discussed. Operations begin at block 600 by selecting a frequency on which an rotatable tag according to embodiments of the present invention will transmit and/or receive. The rotatable tag may wake up from a sleep mode so as to allow the rotatable tag to receive a request (block 605). Once the rotatable tag is awake, the rotatable tag may listen for the request for presence information (block 610). It is determined if a request for presence information has been received from the reader at the rotatable tag within a predetermined period of time when the rotatable tag was awake (block 615). In some embodiments of the present invention, the predetermined period of time may be randomly determined and tracked by a timer included in the rotatable tag. It will be understood that in some embodiments of the present invention the predetermined period of time may be increased if the request for presence information is not received within a second predetermined period of time, greater than the first predetermined period of time.

If is it determined that a request has not been received (block 615), the rotatable tag returns to the sleep mode (block 620) and operations return to block 605 and repeat until a request is received while the rotatable tag is awake. If it is determined that the request has been received (block 615), the requested information may be provided to the reader (block 630). Once the requested information has been provided (block 630), the rotatable tag is returned to sleep mode (block 620) and operations return to block 605 and repeat until another request is received at the rotatable tag.

Figure 7:
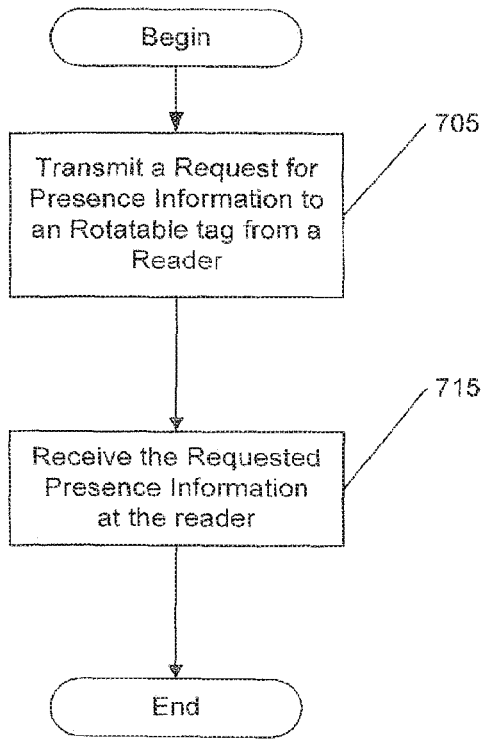

Referring now to FIG. 7, methods for providing location information associated with a mobile device according to further embodiments of the present invention will be discussed. Operations begin at block 705 by transmitting a request for presence information associated with the mobile device from a reader to an rotatable tag associated with the mobile device. The reader may be integrated with an existing outlet and the rotatable tag may be affixed to the mobile device. The requested presence information is received at the reader responsive to the transmitted request from the rotatable tag affixed to the mobile device (block 715).

Figure 8:
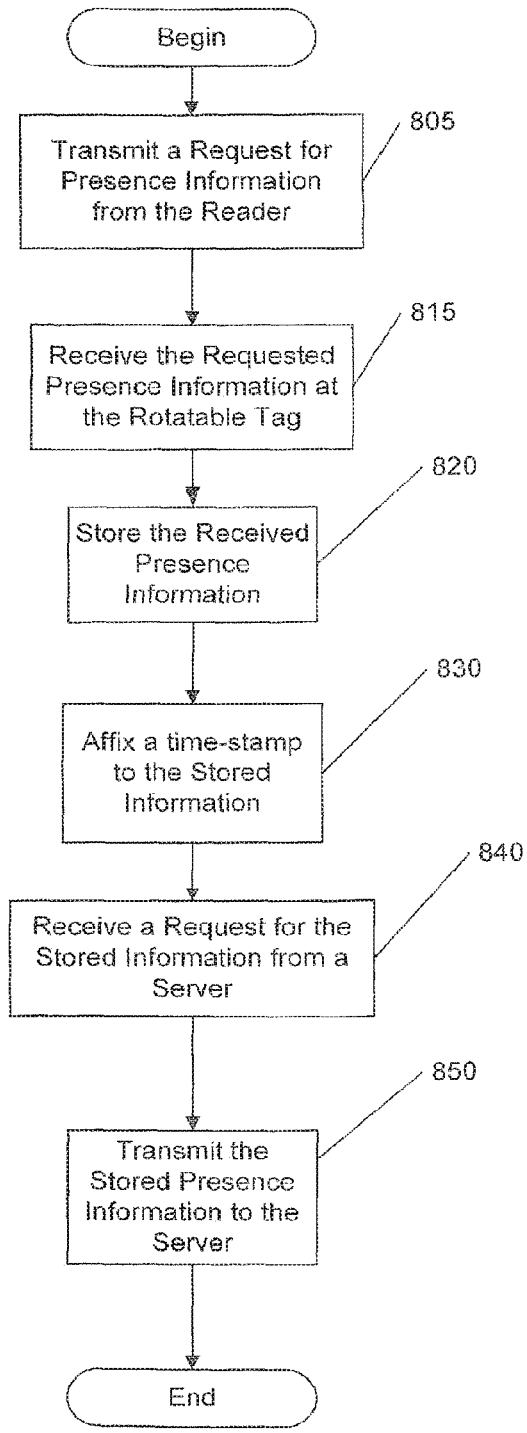

Referring now to FIG. 8, methods for providing location information associated with a mobile device according to some embodiments of the present invention will be discussed. Operations begin at block 805 by transmitting a request for presence information associated with the mobile device from a reader to an rotatable tag associated with the mobile device. In some embodiments of the present invention, the request for presence information may be transmitted multiple times so as to allow receipt at the rotatable tag when the rotatable tag is awake.

The requested presence information is received at the reader responsive to the transmitted request from the rotatable tag affixed to the mobile device (block 815). In some embodiments of the present invention, the reader may receive presence information from more than one rotatable tag responsive to the request. In these embodiments of the present invention, signal strength may be used to determine the relevant rotatable tag from among the plurality of rotatable tags as discussed above.

The received presence information may be stored at the reader (block 820). In some embodiments of the present invention, the presence information may be stored in a FIFO and a time stamp may be affixed to each entry in the FIFO (block 830).

A request may be received, from a server, at the reader for the stored presence information (block 840). The request may be received at the reader over the power lines. The stored presence information may be transmitted to the server from the reader responsive to the received request (block 850). The transmitted information may further include a name of the reader providing the stored information, a temperature of the environment in which the location sits and a current time.

Figure 9:
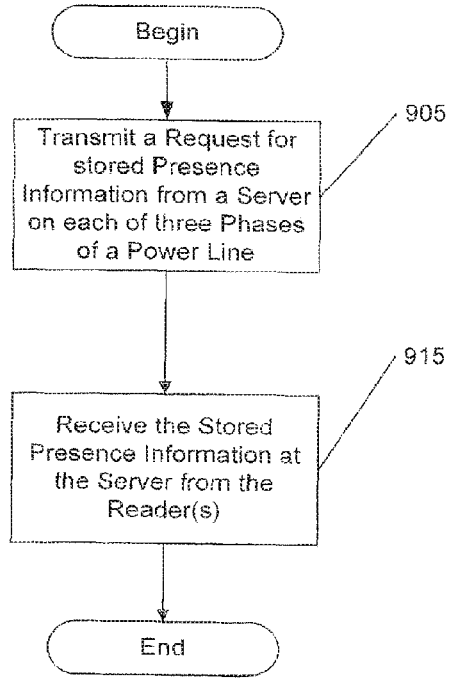

Referring now to FIG. 9, methods for providing location information associated with a mobile device according to further embodiments of the present invention will be discussed. Operations begin at block 905 by transmitting, from a server, a request for location information stored at one or more readers on one of three phases of a power line. In some embodiments of the present invention a power line modem is provided on each of three phases of a power line. Each of the modems may be configured to transmit a request for stored location information simultaneously as discussed in detail with respect to FIG. 2. The stored location information may be received at the server on each of the three phases of the power line responsive to the transmitted request (block 915).

Figure 10:
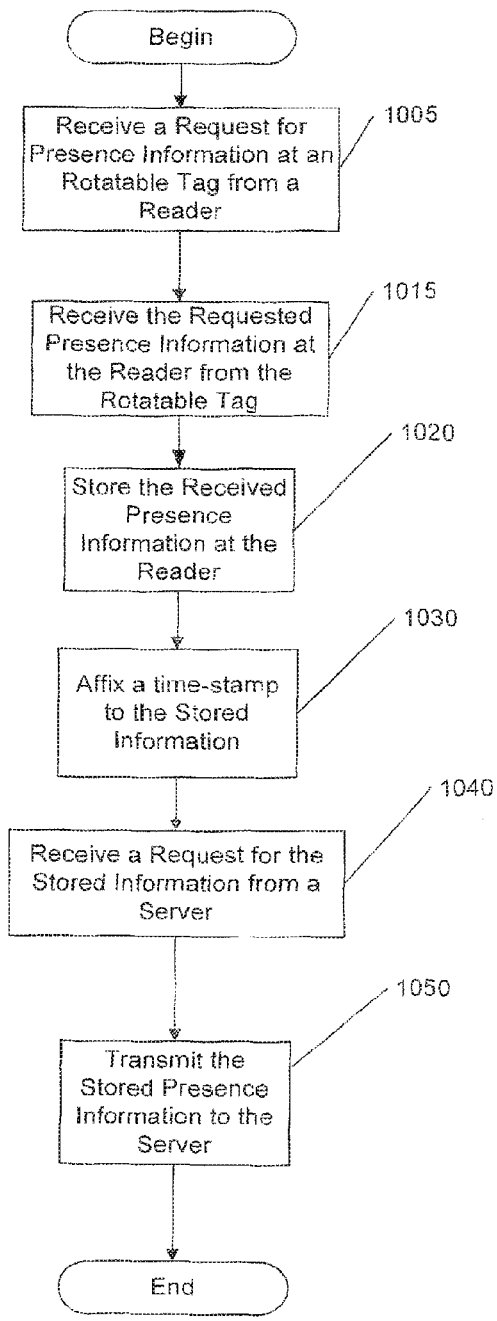

Referring now to FIG. 10, methods for providing location information associated with a mobile device according to still further embodiments of the present invention will be discussed. Operations begin at block 1005 by receiving at an rotatable tag a request for presence information associated with the mobile device from a reader. The requested presence information is received at the reader responsive to the request from the rotatable tag affixed to the mobile device (block 1015). In some embodiments of the present invention, the reader may receive presence information from more than one rotatable tag responsive to the request. In these embodiments of the present invention, signal strength may be used to determine the relevant rotatable tag from among the plurality of rotatable tags as discussed above.

The received presence information may be stored at the reader (block 1020). In some embodiments of the present invention, the presence information may be stored in a FIFO and a time stamp may be affixed to each entry in the FIFO (block 1030).

A request may be received, from a server, at the reader for the stored location/presence information (block 1040). The request may be received at the reader over the power lines. The stored location information may be transmitted to the server from the reader responsive to the received request (block 1050). The transmitted information may further include a name of the reader providing the stored information, a temperature of the environment in which the location sits and a current time.

As discussed briefly above with respect to FIGS. 1A through 10, methods, systems, devices and computer program products according to some embodiments of the present invention may provide improved asset management capabilities.

In the drawings and specification, there have been disclosed embodiments of the invention and, although specific terms are employed, they are used in a generic and descriptive sense only and not for purposes of limitation, the scope of the invention being set forth in the following claims.

What is claimed is:

1. A method, comprising:
receiving, at a tag affixed to a moveable object, a signal to wake the tag affixed to a moveable object;
receiving, at the tag affixed to a moveable object, a request from at least one receiver for presence information associated with the moveable object;
providing, from the tag affixed to a moveable object, identification information associated with the moveable object;
transmitting, from the tag affixed to a moveable object, location data to the at least one receiver;
transmitting, from the tag affixed to a moveable object, use state information associated with the moveable object; and
returning the tag affixed to a moveable object to a sleep state.

2. The method of claim 1, wherein the receiving a signal comprises receiving a signal from a timer included within the tag affixed to a moveable object.

3. The method of claim 2, wherein a time period associated with the timer is variable.

4. The method of claim 3, wherein the time period is based upon a distance of the tag affixed to a moveable object from a receiver.

5. The method of claim 3, wherein the time period is based upon a time of last receipt of a request.

6. The method of claim 3, wherein the time period is varied randomly.

7. The method of claim 1, wherein the receiving a signal comprises receiving a signal from a receiver.

8. The method of claim 1, wherein the use state comprises available for use, in use, needs cleaning and/or needs service.

9. The method of claim 1, wherein the movable object is an infusion pump.

10. The method of claim 1, wherein the tag is intrinsically safe such that it can be used in an oxygen rich environment.

11. The method of claim 1, wherein the tag includes at least one sensor and wherein the at least one sensor comprises a temperature sensor, a motion sensor, a humidity sensor, a gas sensor, a carbon monoxide sensor, an accelerometer or a gyroscope.

12. The method of claim 1, wherein the tag is configured to transmit and/or receive information.

13. The method of claim 1, wherein the movable object is selected from the group consisting of a hospital asset and a patient.

14. The method of claim 13, wherein the use state is a patient state.

15. The method of claim 1, wherein the at least one receiver comprises a receiver located in a hospital.

16. The method of claim 1, wherein the tag affixed to a moveable object comprises a rotatable tag.

* * * * *